United States Patent [19]

Hsia et al.

[11] Patent Number: 5,231,090

[45] Date of Patent: Jul. 27, 1993

[54] TREATMENT FOR HYPERCHOLESTEROLEMIA

[75] Inventors: Sung L. Hsia; Jin L. He, both of Miami, Fla.

[73] Assignee: University of Miami, Miami, Fla.

[21] Appl. No.: 559,932

[22] Filed: Jul. 30, 1990

[51] Int. Cl.$^5$ .................. A61K 31/66; A61K 31/685; A61K 9/70

[52] U.S. Cl. ........................ 514/78; 514/75; 514/77; 514/824; 514/947; 424/449

[58] Field of Search ............ 514/75, 77, 78, 824, 514/947; 424/449

[56] References Cited

U.S. PATENT DOCUMENTS

| | | | |
|---|---|---|---|
| 3,197,371 | 7/1965 | Dailey | 514/78 |
| 3,203,862 | 8/1965 | Jones | 514/78 |
| 4,780,456 | 10/1988 | Pistolesi | 514/78 |

FOREIGN PATENT DOCUMENTS

| | | | |
|---|---|---|---|
| 0180786 | 5/1986 | European Pat. Off. | 514/78 |
| 3437517 | 5/1985 | Fed. Rep. of Germany | 514/78 |
| 0115820 | 9/1980 | Japan | 514/77 |
| 0038215 | 3/1983 | Japan | 514/77 |
| 0097916 | 5/1985 | Japan | 514/78 |
| 0214864 | 10/1985 | Japan | 514/78 |

Primary Examiner—Frederick E. Waddell
Assistant Examiner—Kimberly R. Jordan
Attorney, Agent, or Firm—Cushman, Darby & Cushman

[57] ABSTRACT

The present invention relates to a method of modifying serum cholesterol levels in a mammal by topically administering to the skin of the mammal an effective amount of at least one phospholipid. Atherosclerosis, and related complications, can be treated, or prevented, using the present method.

14 Claims, 4 Drawing Sheets

FIG. 4

No. of rabbits: 7    Mean + SD mg/dl

| | Total serum | HDL | LDL | VLDL |
|---|---|---|---|---|
| Before treatment | 102.86 ±38.6 | 51.03 ±12.56 | 37.47 ±26.93 | 14.36 ±7.80 |
| 1 week after treatment | 94.77 ±37.4 | 55.47 ±17.38 | 19.29 ±13.64 | 20.0 ±10.26 |
| 2 weeks after treatment | 91.8 ±36.5 | 58.24 ±19.28 | | |
| 3 weeks after treatment | 88.7 ±39.7 | 63.9 ±19.05 | 13.96 ±18.06 | 10.8 ±10.5 |
| p value between data before & 3 weeks after treatment | 0.049 | 0.056 | 0.017 | 0.516 |

TREATMENT FOR HYPERCHOLESTEROLEMIA

BACKGROUND OF THE INVENTION

1. Technical Field

The present invention relates, in general, to hypercholesterolemia and, more specifically, to the use of phospholipids in a method of modifying blood cholesterol levels.

2. Background Information

Elevated blood cholesterol level is a major risk factor for the development of coronary heart disease, stroke and peripheral vascular disease. Of these, coronary heart disease has remained the leading cause of death in the United States and other affluent countries, in spite of recent advances in the management of the disease and understanding of the disease mechanism. It is understood that the underlying cause of the above-mentioned diseases is atherosclerosis, an insidious process of deposition of cholesterol and its esters, compounded with other materials, in characteristic plaques in the arterial wall.

Lowering blood cholesterol can reduce the risk of coronary heart disease (Stamler et al., JAMA 256:2823, 1986; The Lipid Research Clinics Coronary Primary Prevention Trial Results, I: Reduction in incidence of coronary heart disease. JAMA 251:351, 1984; The Lipid Research Clinics Coronary Primary Prevention Trial Results, II: The relation of reduction in incidence of coronary heart disease to cholesterol lowering. JAMA 251:365, 1984). In fact, each one percent reduction in blood cholesterol level is believed to result in approximately a two percent reduction in coronary heart disease rate (National Institutes of Health, Consensus Development Conference Statement. Vol. 5, No. 7).

Recommended methods for lowering blood cholesterol include reducing weight, increasing exercise, and altering diet by lowering cholesterol intake and substituting saturated fat with polyunsaturated fat. The effectiveness and drawbacks of several drugs that have been approved by FDA for use in the treatment of hypercholesterolemia have been recently reviewed (Blum et al., JAMA 261:3582, 1989).

Cholesterol and phospholipids are essential components of cellular organelles and membranes of animals. They are also major components of lipoproteins of the circulating blood. Their simultaneous occurrence in animal tissues indicates an affinity between molecules of phospholipids and cholesterol. This affinity has been utilized in the technology for preparing liposomes. Liposomes prepared from phospholipids, which are notoriously unstable, can be stabilized by the addition of cholesterol.

The affinity of phospholipids for cholesterol provides a basis for the hypothesis that phospholipids, when properly administered, could remove cholesterol from atherosclerotic plaques, and thus reduce the risk for coronary heart disease. Indeed, in experimental animals, intravenous administration of phospholipids has resulted in resolution of atherosclerotic lesions (Friedman et al., Proc. Soc. Exp. Biol. Med. 95:580, 1957; Howard et al., Atherosclerosis 14:17, 1971; Stafford et al., Artery 1(2):105, 1975). Extensive changes in serum lipoproteins in rabbits after intravenous injection of liposomes made of egg yolk phospholipids have been demonstrated. Such changes may have anti-atherogenic effects (Mendez et al., Lipids 23:961, 1988).

Although the above-described results suggest potential usefulness of phospholipids in the prevention and treatment of atherosclerosis, intravenous injection is an invasive method of drug delivery, and has objectionable features The development of a more convenient method for delivering phospholipids, and thereby effecting a reduction in blood cholesterol levels, is needed. The present invention provides such method.

SUMMARY OF THE INVENTION

It is a general object of the invention to provide a convenient method for effecting modification of serum cholesterol levels.

It is a specific object of the invention to provide a method of preventing and treating atherosclerosis, and related complications.

Various other objects and advantages of the present invention will become obvious from the drawings and description of the invention that follow.

The present invention relates to a method of lowering serum cholesterol levels in a mammal. The method comprises topically administering to a mammal an amount of a phospholipid-containing composition sufficient to reduce serum cholesterol to an acceptable level.

BRIEF DESCRIPTION OF THE DRAWINGS

FIG. 4 summarizes the effects of topical application of a phospholipid solution on cholesterol levels.

DETAILED DESCRIPTION OF THE INVENTION

Figure 1:
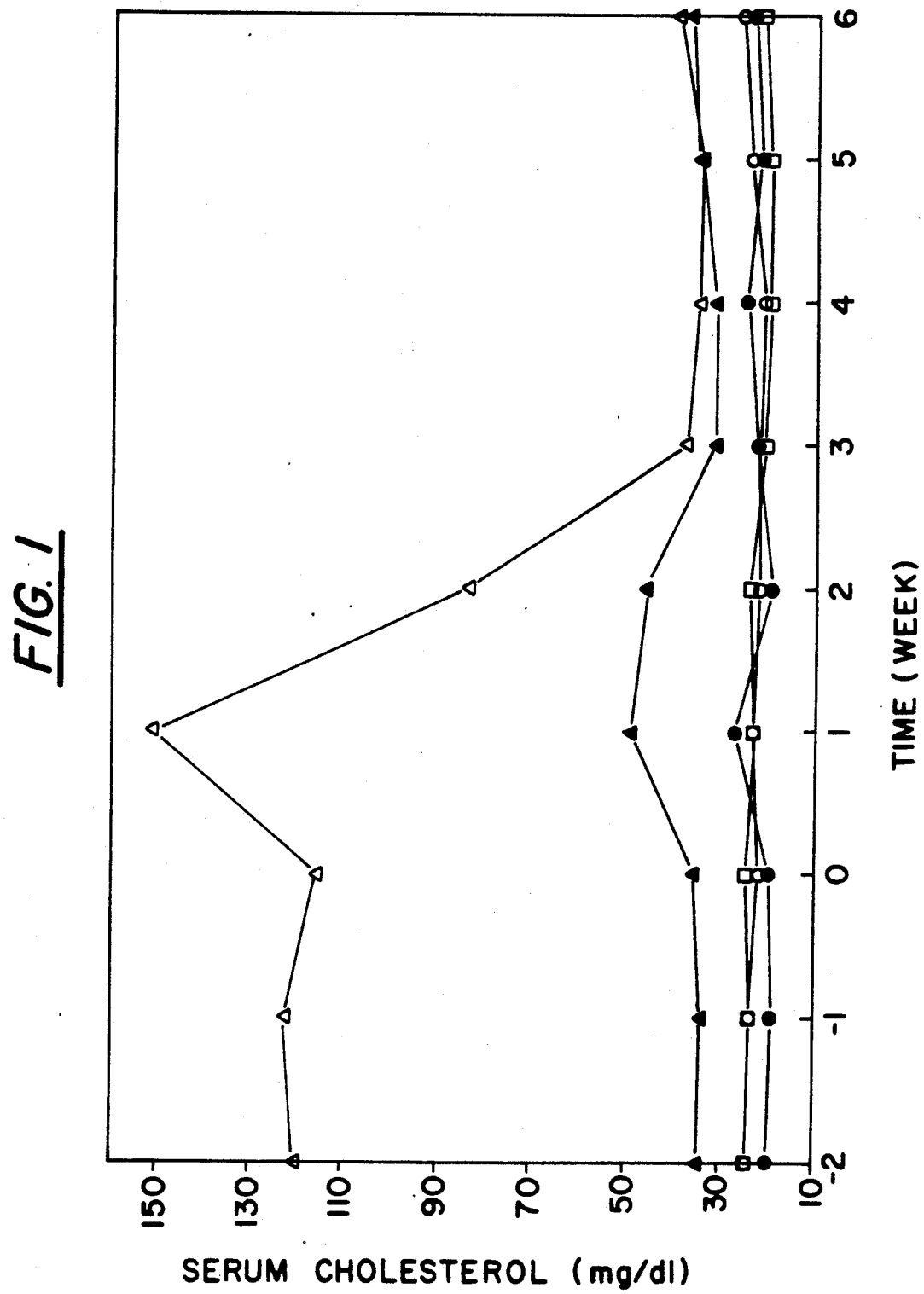
FIG. 1 shows the response in serum cholesterol level to the topical application of a phospholipid solution to the skin of 5 rabbits.

The present invention relates to a method of lowering serum cholesterol levels in mammals. The method comprises topically administering to the mammal an amount of a phospholipid-containing composition sufficient to lower serum cholesterol to an acceptable level. The present invention is further directed to a method of preventing and treating atherosclerosis, and related complications, by topically administering to a mammal a phospholipid-containing composition in an amount sufficient to lower the serum cholesterol level of the mammal. The methods of the present invention result in the lowering of serum LDL cholesterol levels and the enhancing of serum HDL cholesterol levels in the mammal undergoing treatment.

Phospholipid-containing compositions suitable for use in the present method comprise at least one phospholipid in a concentration of between, for example, 5% and 50% (w/v). Any natural or synthetic phospholipid, lecithin (phosphatidylcholine), phosphatidylethanolamine and phosphatidylserine, having an affinity for cholesterol can be used in the composition, however, lecithin is preferred.

Also included in compositions suitable for use in the present invention is a pharmaceutically acceptable carrier The carrier is, advantageously, an alcohol, such as ethanol, however, any carrier that does not affect the affinity of the phospholipid for cholesterol can be used.

Other possible carriers include isopentenyl, isobutyl or isopropyl alcohol.

One of ordinary skill in the art can readily determine the appropriate amount of the phospholipid-containing composition to be administered to a particular patient to achieve the appropriate reduction in serum cholesterol level. In one embodiment, about 25 ml of a 25% phospholipid/ethanol solution is applied 1 or 2 times per week.

The phospholipid-containing composition to be used in the present method can be rubbed onto or sprayed onto the skin of the individual whose serum cholesterol is sought to be altered. Alternative forms of topical administration can also be used. For example, the phospholipid-containing composition can be present in a patch which can be adhered to the skin of the individual in a manner such that topical administration is effected.

In addition to active ingredient (phospholipid) and carrier, other ingredients that confer desirable characteristics on the composition can also be included in the formulation (i.e., perfumes, coloring agents, water, absorption enhancers, etc.).

The present invention is described in further detail in the following non-limiting Examples.

EXAMPLE I

New Zealand white rabbits usually have a serum cholesterol level in the range of 30-50 mg/dl. By chance, an experimental rabbit (R4) spontaneously developed hypercholesterolemia, with a serum cholesterol level of 110 mg/dl.

New Zealand white rabbits were fed normal rabbit chow and maintained at a controlled temperature with a 12 hour dark/light cycle. Food was removed from the rabbits at least 12 hours prior to collection of blood samples from the ear vein.

Phospholipid was extracted from egg yolk by standard procedures and purified. The phospholipid solution was prepared by adding ethanol to the purified phospholipids to a final concentration of 25-50% (w/v).

Figure 2:
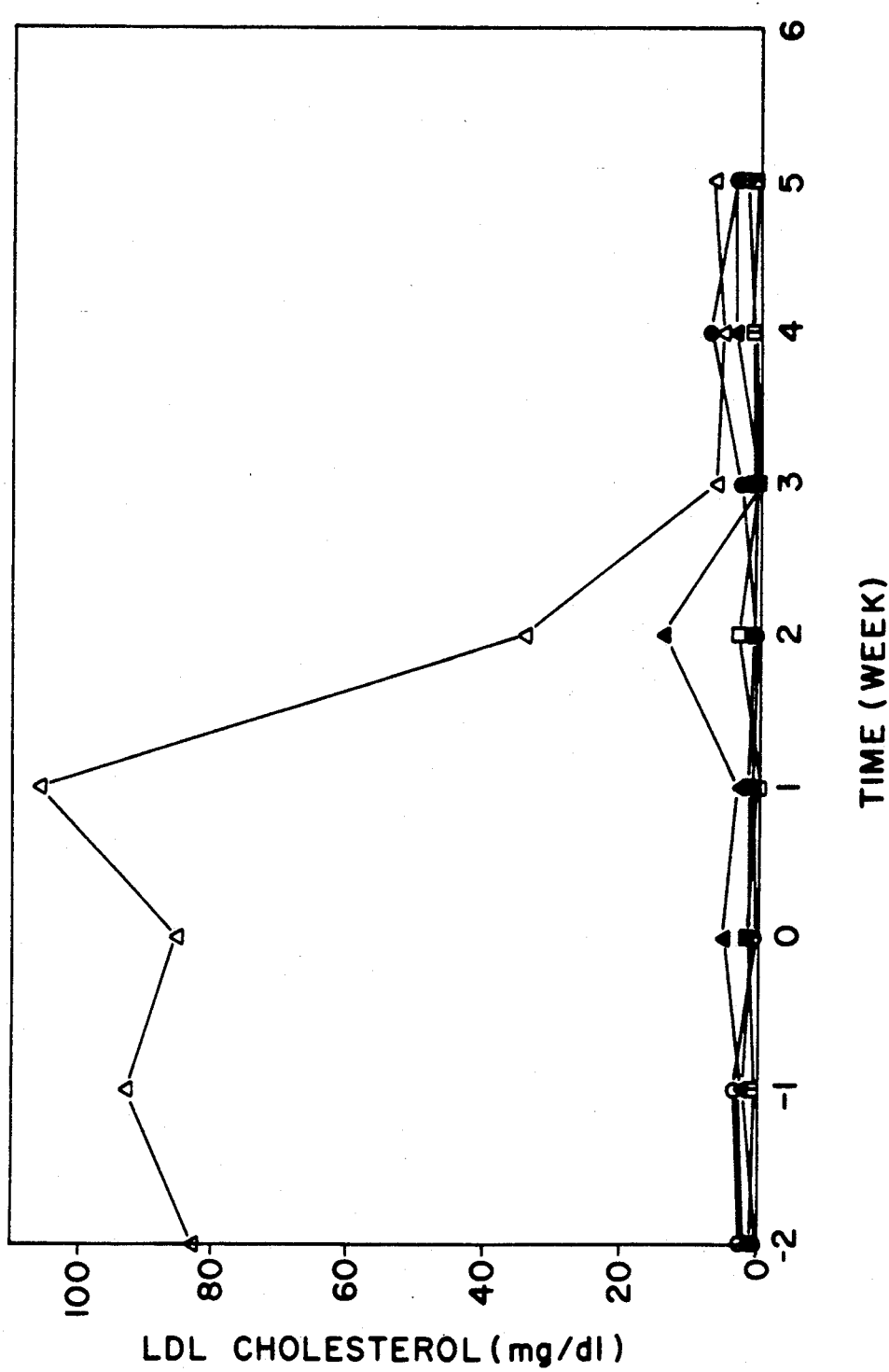
FIG. 2 shows the response in LDL cholesterol level to the topical application of a phospholipid solution to the skin of 5 rabbits.
Figure 3:
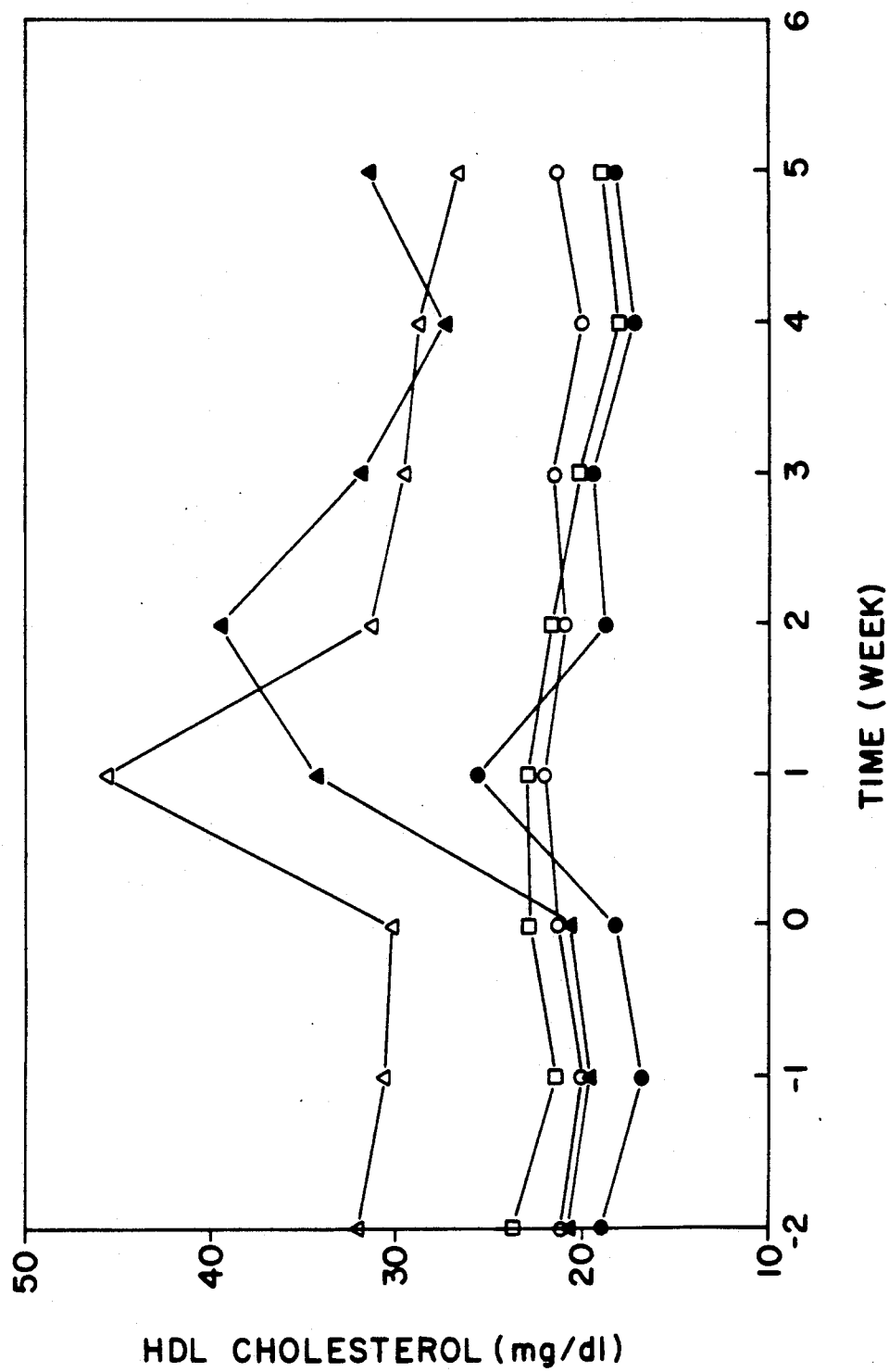
FIG. 3 shows the response in HDL cholesterol level to the topical application of a phospholipid solution to the skin of 5 rabbits.

To test whether topically applied phospholipids can lower serum cholesterol, the backs of R4 and four other rabbits (R1, R2, R3 and R5) were shaved, and 3 ml of a solution of 25% (w/v) egg yolk phospholipids in ethanol were applied to the shaved skin of R3, R4 and R5, while 3 ml of ethanol alone was applied to the controls (R1 and R2). Blood samples were taken weekly from all rabbits, 2 weeks before the application and 6 weeks thereafter, and again at the end of the 10th week. Cholesterol was assayed in serum, high density lipoproteins (HDL) and low density lipoproteins (LDL) by established procedures. The results are shown in FIGS. 1-3.

The data show that in the control animals (R1 and R2) cholesterol levels held steady throughout the experimental period. In contrast, data from R4 show dramatic drops in serum and LDL cholesterol, and also an increase of HDL, 3 weeks after topical application of phospholipids.

The response from R5 whose serum cholesterol was slightly elevated, was less dramatic. The data show little or no effect on serum cholesterol and lipoproteins in R3 which had low serum cholesterol.

The above experiment was repeated with 7 more rabbits having serum cholesterol levels above 100 mg/dl. These animals were selected from 120 rabbits after their serum cholesterol levels were measured.

The results of the 7 rabbits after topical treatment with phospholipids are shown in FIG. 4. A decrease in serum and LDL cholesterol and an increase in HDL cholesterol were observed 3 weeks after the treatment.

The decrease in serum cholesterol, and especially the decrease in LDL cholesterol, are thought to be desirable in terms of the prevention of atherosclerosis. The increase of HDL cholesterol, which has been labeled as "good cholesterol" in the lay press, is of importance not only in reducing the risk of atherosclerosis but also for reversal of the disease process. These findings form the basis for the prevention and treatment of atherosclerotic diseases in humans by topical treatment with phospholipids.

EXAMPLE II

RJH, a 62 year old man who was in apparent good health, although having a long history of elevated serum cholesterol and triglyceride levels, volunteered to test the effect of topical lecithin on serum cholesterol. A fasting blood sample was drawn on day 1 and on day 8 for the measurements of serum cholesterol and triglycerides, and cholesterol in the low density lipoproteins (LDL), very low density lipoproteins (VLDL) and high density lipoproteins (HDL) by standard procedures. The results showed that his serum lipid levels were steadily elevated (see table). In the evening of day 8, he applied 25 ml of a 50% solution of egg lecithin (purified according to procedures published in the Journal of the American Oil Chemists Society (42:53-56 (1965)) in ethanol to cover most of his body surface. He experienced no ill effects in follow up.

Fasting blood samples were drawn from RJH on day 15 and day 23 for lipid measurements. The results showed decreases in serum and LDL cholesterol after the treatment with topical lecithin. The 16.8% drop of LDL cholesterol from 191 to 159 mg/dl in 2 weeks after the treatment was especially remarkable. The data are summarized in the following table:

| RJH LIPID PROFILE (mg/dl of serum) | | | | | |
|---|---|---|---|---|---|
| DAY | SC | TG | HDL | VLDL | LDL |
| 1 | 250 | 241 | 49 | 11 | 190 |
| 8 | 254 | 156 | 49 | 14 | 191 |
| 8 | Treatment with topically applied lecithin. | | | | |
| 15 | 246 | 172 | 52 | 10 | 184 |
| 23 | 234 | 188 | 51 | 24 | 159 |

Abbreviations are: SC, Serum cholesterol; TG, serum triglycerides; HDL, high density lipoproteins; VLDL, very low density lipoproteins; LDL, low density lipoproteins.

EXAMPLE III

BK, a 39 year old man who was in apparent good health although slightly overweight, became concerned about his elevated serum cholesterol level. Fasting blood samples were taken in three consecutive weeks, and the results showed serum cholesterol consistently above 290 mg/dl. He was given the following instruction:

1) Take a hot shower in the evening, and dry your skin with a towel.
2) Apply the solution given to you to your skin and rub it in well, to cover your legs, arms, the abdomen and the back. Use all the solution, and spread it to cover all your body.

3) To enhance percutaneous absorption, wrap your legs with a thin plastic film, e.g. Saran Wrap, and fix the wrapping with a tape or an Ace bandage.

4) Rest or take a nap, and wait for at least 2 hours before washing off the unabsorbed material on your skin.

The solution given him for each application was 12.5 ml of Formula M-23-90 which has the following composition:

| Formula M-23-9 | (Total volume 78 ml) |
|---|---|
| Soy lecithin | 25 gm |
| BHT | 0.2 gm |
| Ethanol | 25 ml |
| Isopropanol | 18 ml |
| Distilled water | 18 ml |

BK returned each week or 10 days for analysis of fasting blood lipid profile. His serum cholesterol and low density lipoproteins showed definite reductions after each treatment with Formula M-23-90. He reported no undesirable effects. A summary of his lipid profiles is shown in the following table

| Day | SC | TG | HDL | VLDL | LDL |
|---|---|---|---|---|---|
| | | BK LIPID PROFILE | | | |
| | | (mg/dl of serum) | | | |
| 1 | 292 | 356 | 34 | 98 | 160 |
| 9 | 295 | 311 | 42 | 108 | 145 |
| 16 | 294 | 167 | 40 | 56 | 198 |
| 16 | Treatment with Formula M-23-90 | | | | |
| 24 | 262 | 263 | 35 | 52 | 175 |
| 24 | Treatment with Formula M-23-90 | | | | |
| 35 | 242 | 248 | 37 | 81 | 124 |
| 35 | Treatment with Formula M-23-90 | | | | |
| 42 | 236 | 257 | 38 | 72 | 126 |

Abbreviations are: SC, serum cholesterol; TG, serum triglycerides; HDL, high density lipoproteins; VLDL, very low density lipoproteins; LDL, low density lipoproteins.

The entire contents of all references cited hereinabove are hereby incorporated by reference.

While the foregoing invention has been described in some detail for purposes of clarity and understanding, it will be clear to one skilled in the art from a reading of this disclosure that various changes in form and detail can be made without departing from the true scope of the invention.

What is claimed is:

1. A method of increasing the ratio of high density lipoprotein to low density lipoprotein in the serum of a mammal, which comprises topically administering to said mammal an amount of a phospholipid sufficient to increase said ratio.

2. The method according to claim 1, wherein said ratio is increased by lowering the level of low density lipoprotein cholesterol.

3. The method according to claim 1, wherein said ratio is increased by enhancing the level of high density lipoprotein cholesterol.

4. The method according to claim 1, wherein said phospholipid is lecithin.

5. The method according to claim 1, wherein said phospholipid is phosphatidylserine.

6. The method according to claim 1, wherein said phospholipid is phosphatidylethanolamine.

7. The method according to claim 1, wherein said phospholipid is present as a liquid solution.

8. The method according to claim 7, wherein said phospholipid is present as an alcohol solution.

9. The method according to claim 8, wherein said alcohol is ethanol.

10. The method according to claim 1, wherein said phospholipid is present in a composition having the form of a lotion, cream, gel or ointment.

11. The method according to claim 1 wherein said phospholipid is soy lecithin administered in combination with butylated hydroxytoluene, ethanol, isopropanol and distilled water.

12. A transdermal patch comprising a reservoir containing an amount of a phospholipid sufficient to increase the ratio of high density lipoprotein to low density lipoprotein in the serum of a mammal
wherein said patch is constructed such that said phospholipid is available for transdermal administration to a mammal wearing said patch.

13. A method of lowering the serum cholesterol level of a mammal which comprises typically administering to said mammal an amount of a phospholipid sufficient to effect said lowering.

14. A method of treating atherosclerosis, and related complications, which comprises topically administering to a patient in need of such treatment an amount of a phospholipid sufficient to treat atherosclerosis and said related complications.

* * * * *